United States Patent
Rhee et al.

[11] Patent Number: 6,103,729
[45] Date of Patent: *Aug. 15, 2000

[54] CATHECOL DERIVATIVES AND A METHOD FOR THE PREPARATION THEREOF AND A PHARMACEUTICAL COMPOSITION CONTAINING THE SAME

[75] Inventors: Chung Keun Rhee, Seoul; Myung Xik Xiang, Kyungkee-do; Byoung Chool Suh, Seoul; Kwang Hyuk Lee, Kyungkee-do; Youn Ha Lee, Kyungkee-do; Young Gi Kim, Seoul, all of Rep. of Korea

[73] Assignee: Cheil Jedang Corp., Seoul, Rep. of Korea

[*] Notice: This patent issued on a continued prosecution application filed under 37 CFR 1.53(d), and is subject to the twenty year patent term provisions of 35 U.S.C. 154(a)(2).

[21] Appl. No.: 08/931,303

[22] Filed: Sep. 16, 1997

[30] Foreign Application Priority Data

Nov. 28, 1996 [KR] Rep. of Korea ............ 96-58701
Apr. 25, 1997 [KR] Rep. of Korea ............ 97-15476
Jun. 27, 1997 [KR] Rep. of Korea ............ 97-27909

[51] Int. Cl.[7] ............ A61K 31/519; C07D 487/22
[52] U.S. Cl. ............ 514/262; 544/265; 544/276
[58] Field of Search ............ 549/69; 514/447, 514/265, 276, 262

[56] References Cited

U.S. PATENT DOCUMENTS 5,698,711   12/1997   Palfreyman ............ 549/66

FOREIGN PATENT DOCUMENTS

98/23620   6/1998   WIPO .

*Primary Examiner*—Mukund J. Shah
*Attorney, Agent, or Firm*—Burns, Doane, Swecker & Mathis, L.L.P.

[57] ABSTRACT

A phosphodiesterase IV inhibiting cathecol derivatives of the general formula I:

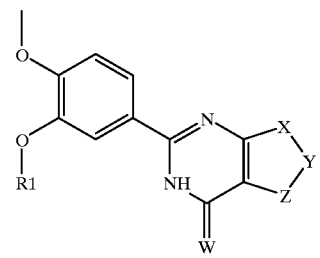

Formula I or a pharmaceutically acceptable salt thereof in which R1 is $C_{1-7}$ alkyl; $C_{3-7}$ cycloalkane; phenyl optionally substituted with lower alkyl lower alkoxy, nitro or halogen; pyrimidine optionally substituted with lower alkyl, lower alkoxy, nitro or halogen; or pyridine optionally substituted with lower alkyl, lower alkoxy, nitro or halogen; X, Y and Z are each independently oxygen, nitrogen or sulfur optionally substituted with $C_{1-7}$ alkyl, $C_{3-7}$ cycloalkane or phenyl; W is oxygen or sulfur is disclosed. In addition, a process for producing the compound of the general formula I and a pharmaceutical composition containing pharmaceutically effective amount of the compound of the general formula I are disclosed.

4 Claims, No Drawings

CATHECOL DERIVATIVES AND A METHOD FOR THE PREPARATION THEREOF AND A PHARMACEUTICAL COMPOSITION CONTAINING THE SAME

FIELD OF THE INVENTION

The present invention relates to novel cathecol derivatives useful in prevention or treatment of respiratory system related diseases, for example bronchial asthma, by inhibiting the enzymatic activity of phosphodiesterase IV. Also, the present invention relates to a method for producing the said compounds and a pharmaceutical composition containing the said compounds.

BACKGROUND OF THE INVENTION

Bronchial asthma is a complex, multifactorial disease characterized by reversible narrowing of the airway and hyperreactivity of the respiratory tract to external stimuli. Therapeutic agents for asthma are classified into drug for directly relaxing the contraction of the airway or drug for anti-inflammatory action and, for example, include β-2 antagonist, steroids, phosphodiesterase inhibitor, muscarinic antagonist, mucosa, et al.

Phosphodiesterase IV is an enzyme that specifically hydrolyzes cAMP(adenosine 3',5'-cyclic monophosphate) into inactive adenosine 3',5'-mono-phosphate. The cAMP has been shown to be a second messenger mediating the cellular responses to external stimuli and to function to relax or contradict bronchial muscles.

The inhibition of phosphodiesterase IV leads to prevention of broncospasm by maintaining the concentration of cAMP and also induces an anti-inflammation. Therefore, compounds that inhibit phosphodiesterase IV should be effective in treating asthma and the like diseases.

EP Publication No. 232,199 B1 discloses phosphodiesterase IV-inhibiting phenyl derivatives useful in treatment of allergic and inflammatory disease, which are represented as follows.

WO92/12961 discloses compounds of the following formula, which inhibit adenosine cyclic phosphate phosphodiesterase. However, WO92/12961 does not mention any inhibitory activity of TNF by the said compounds.

EP Publication No. 497,564 A1 discloses compounds effective in inhibiting adenosine cyclic 3',5'-phosphate phosphodiesterase IV, which are represented as follows:

SUMMARY OF THE INVENTION

In one aspect, the present invention provides a compound of the general formula I:

Formula I or a pharmaceutically acceptable salt thereof in which

R1 is $C_{1-7}$ alkyl; $C_{3-7}$ cycloalkane; phenyl optionally substituted with lower alkyl, lower alkoxy, nitro or halogen; pyrimidine optionally substituted with lower alkyl, lower alkoxy, nitro or halogen, or pyridine optionally substituted with lower alkyl, lower alkoxy, nitro or halogen;

X, Y and Z are each independently oxygen, nitrogen or sulfur optionally substituted with $C_{1-7}$ alkyl, $C_{3-6}$ cycloalkane or phenyl, W is oxygen or sulfur.

In another aspect, the present invention provides a process for producing the above compound of the general formula I.

In still another aspect, the present invention provides a pharmaceutical composition comprising pharmaceutically effective amount of the present compound of the general formula I or pharmaceutically acceptable salt thereof and a pharmaceutically acceptable carrier.

DETAILED DESCRIPTION OF THE INVENTION

The preferred compounds of the present invention are those wherein R1 is methyl or cyclopentyl; a) X=CH, Y=CH and Z=S, b) X=N, Y=CH and Z=NR2, c) X=CH, Y=N and Z=NR2, d) X=NR2, Y=N and Z=N or e) X=N, Y=N and Z=NR2, in which each R2 is $C_{1-6}$ alkyl, $C_{3-6}$ cycloalkane or phenyl; W is oxygen.

The more preferred compounds of the present invention are as follows:

3-(3-cyclopentyloxy-4-methoxyphenylcarboxylamido)-1H-4-pyrazolecarboxylamide.

4-(3-cyclopentyloxy-4-methoxyphenylcarboxylamido)-1H-4-imidazole-5-carboxylamide.

3-(3-cyclopentyloxy-4-methoxyphenylcarboxylamido)-2-thiophenecarboxylamide.

2-(3-cyclopentyloxy-4-methoxyphenyl)-3,4-dihydroyhieno[3,4-d]pyrimidine-4-one;

2-(3-cyclopentyl-4-methoxyphenyl)-6,7-dihydro-1H-6-purinone;

5-(3-cyclopentyloxy-4-methoxyphenylcarboxylamido)-6,7-dihydro-1H-pyrazolo[4,3-d]pyrimidine-7-one;

2-(3-cyclopentyloxy-4-methoxyphenyl)-3,4-dihydro-4-quinazolinone; and 3-(3,4-dimethoxyphenylcarboxylamido)-3,4-dihydro-4-quinazolinone.

The process for producing the compound of the general formula I according to the present invention comprises the following steps:

(a) reacting a carboxylamide compound of the general formula III:

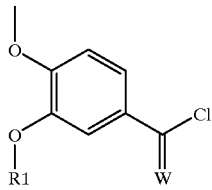

Formula III in which R1 and W represent the same as defined above, with a aminocarboxylamide compound of the general formula IV:

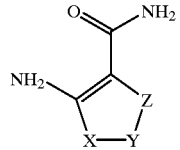

Formula IV in which X, Y and Z represent the same as defined above, to produce a carboxylamide compound of the general formula II:

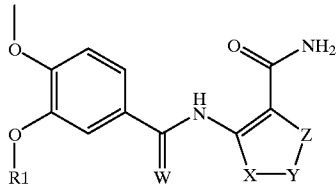

Formula II in which R1, X, Y, Z and W represent the same as defined above, and (b) cyclizing the compound of the general formula II to produce the compound of the general formula I.

The above compound III was obtained by known method (J. Med. Chem. 1994, 37, 1696). The aminocarboxylamide compound IV is commercially available. The cyclization of the above intermediate compound II was carried out by known method (Bioorg. Med. Chem. Lett., 1996, 6, 1819).

For use in medicine, the compounds of the present invention are usually administered as a standard pharmaceutical composition. Therefore, the present invention provides in a further aspect pharmaceutical compositions comprising a novel compound of formula I or a pharmaceutically acceptable salt thereof and a pharmaceutically acceptable carrier.

The compounds of formula I may be administered by any convenient method, for example by oral, parenteral, buccal, sublingual, nasal, rectal or transdermal administration and the pharmaceutical compositions adapted accordingly.

The compounds of formula I and their pharmaceutically acceptable salts which are active when given orally can be formulated as liquids, for example syrups, suspensions or emulsions, tablets, capsules and lozenges.

A liquid formulation will generally consist of a suspension or solution of the compound or physiologically acceptable salt in a suitable liquid carrier, for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, cellluoses, silicates or oils and the dispersion or suspension then filled into a soft gelatin capsule.

Typical parenteral compositions consist of a solution or suspension of the compound or physiologically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent fust prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdernal administration include ointments, gels and patches.

Preferably the composition is in unit dose form such as a tablet, capsule or ampoule.

The invention will now be described with reference to the following illustrative Examples.

EXAMPLES

Reference Example 1
3-Cyclopentyloxy-4-methoxybenzylaldehyde 50 g of isovanillin was added dropwise to 300 ml of dimethylformamide and, then, 70 g of anhydrous potassium carbonate and 1.5 g of potassium iodide were added to form a supension. The suspension was stirred at 65° C. for 30 minutes. 63 g of cyclopentyl bromide was added dropwise to the suspension over 1 hour and was stirred at 65° C. for 1 day. After cooling to room temperature, the suspension was diluted by adding 1 L of toluene and, then, was washed with 1 N sodium hydroxide (2×5 ml) and distilled water (2×250 ml) in succession. The organic layer was dried over anhydrous sodium sulfate and was concentrated under reduced pressure to obtain 58 g of the title compound (yield: 80%).

$^1$H NMR(CDCl$_3$, δ): 9.84(1H,s), 7.42(2H,m), 6.94(1H,D, J=9 Hz), 4.87(1H,m), 3.93 (3H,s), 2.1–1.6(8H,m)

Reference Example 2
3-Cyclopentyloxy-4-methoxybenzoic Acid 35 g of sulfamic acid was added dropwise to a solution of 58 g of 3-cyclopentyloxy-4-methoxybenzylaldehyde in 450 ml of 80% acetic acid. Then, a solution of 30 g of 80% sodium chloride in 450 ml of distilled water was added dropwise to the suspension over 1 hour while maintaining the reaction temperature to 18° C.–20° C. The reaction solution was stirred for 1 hour and was diluted by adding dropwise 450 ml of distilled water over 30 minutes. The solution was filtered with distilled water and was dried to obtain 56 g of white solid title compound (yield: 90%).

$^1$H NMR(CDCl$_3$, δ): 7.73(1H,dd,J=9,1 Hz), 7.24(2H,d, J=1 Hz), 6.92(1H,d,J=9 Hz), 4.84(1H,m), 3.93(3H,s), 2.1–1.6(8H,m)

Reference Example 3
3-Cyclopentyloxy-4-methoxybenzoic Acid Chloride 54 g of 3-cyclopentyloxy-4-methoxybenzoic acid was added to 30 ml of thiochloride and was stirred for 5 hours. 50 ml of toluene was added to the reaction solution and was concentrated under reduced pressure to obtain 58 g of the dense brown title compound (yield: 98%).

$^1$H NMR(CDCl$_3$, δ): 7.82(1H,dd,J=9,1 Hz), 7.53(1H,d, J=1 Hz), 6.92(1H,d,J=9 Hz), 4.9–4.8(1H,m), 3.87(3H,s), 2.1–1.9(2H,m), 1.9–1.7(4H,m), 1.7–1.5(2H,m)

Reference Example 4
3,4-dimethoxybenzylaldehyde 5 g of isovanillin was added dropwise to 30 ml of dimethylformamide and, then, 7 g of anhydrous potassium carbonate and 0.7 g of potassium iodide were added to form a supension. Then, 0.7 g of methyl bromide was added dropwise to the suspension over 1 hour and was stirred at 65° C. for 1 day. After cooling to room temperature, the suspension was diluted by adding 1 L of toluene and was washed with 1 N sodium hydroxide (2×500 ml) and distilled water (2×250 ml) in succession. The organic layer was dried over anhydrous sodium sulfate and was concentrated under reduced pressure to obtain 5 g of the title compound (yield: 82%).

$^1$H NMR(CDCl$_3$, δ): 7.87(1H,dd,J=9,1 Hz), 7.58(1H,d, J=1 Hz), 6.95(1H,d,J=9 Hz), 3.94(3H,s), 3.82(3H,s)

Reference Example 5
3-(Exo-bicycle[2,2,1]hectyl-2-oxy)-4-methoxybenzylaldehyde 6.8 g of isopropylazocarboxylate was added dropwise to a solution of 5 g of isovanillin, 2.5 g of endo-2-nobonol and 8.8 g of triphenylphosphate in 50 ml of tetrahydrofuran. The reaction solution was refluxed for 48 hours, cooled to room temperature and added dropwise to 250 ml of distilled water. The solution was extracted with ether (3×50 ml) and, then, was washed with distilled (2×50 ml), 1N sodium hydroxide (2×50 ml) and sodium chloride (50 ml) in succession. The organic layer was dried over anhydrous sodium sulfate and was concentrated under reduced pressure. Column chromatography affored 4.2 g of the title compound (yield: 75%).

$^1$H NMR(CDCl$_3$, δ): 9.83(1H,s), 7.43(1H,dd,J=9,1 Hz), 7.35(1H,d,J=1 Hz), 6.96(1H, d,J=9 Hz), 4.28(1H,d,J=6 Hz), 3.93(3H,s), 2.54(1H,d,J=5 Hz), 2.34(1H,t,J=3 Hz), 1.9–1.1 (8H,m)

Reference Example 6
3-(3-cyclopentyloxy-4-methoxyphenylcarboxylamido)-2-thiophenylcarboxylamide 10 ml of pyridine was added dropwise to 700 mg of 3-amino-2-tliophenylcarboxylamide to form a dispension. Then, 1.5 g of 3-cyclopentyloxy-4-methoxybenzoic acid chloride was added dropwise to the suspension and was stirred at room temperature for 1 day. The reaction solution was concentrated under reduced pressure, diluted with chloroform and washed with 1N hydrochloric acid, saturated sodium bicarbonate and sodium chloride in succession. The organic layer was dried and was distilled under reduced pressure. Column chromatography affored 1.1 g of the title compound.

$^1$H NMR(DMSO-d$_6$, δ): 12.42(1H,brs), 8.11(1H,d,J=5,5 Hz), 7.84(1H,d,J=5.5 Hz), 7.51(1H,dd,J=8.5, 2 Hz), 7.45 (1H,d,J=2 Hz), 7.14(1H,d,J-8.5 Hz), 5.0–4.8(1H,m), 3.84 (3H,s), 2.1–1.9(2H,m), 1.9–1.7(4H,m), 1.7–1.6(2H,m)

Reference Example 7
2-(3,4-dimethoxyphenylcarboxamido)benzamide 10 ml of pyridine was added dropwise to 2-aminobezamide to form a dispension. Then, 1 g of 3,4-dimethoxy-1-benzenecarbonyl chloride obtained by Reference Examples 2 and 3 was added dropwise to the suspension and stirred at room temperature for 1 day. The reaction solution was concentrated under reduced pressure, diluted with chloroform and washed with 1N hydrochloric acid, saturated sodium bicarbonate and sodium chloride in succession. The organic layer was dried and concentrated under reduced pressure. Column chromatography affored 900 mg of the title compound.

$^1$H NMR(400 MHz) 12.20(1H,brs), 8.12(1H,d,J=7 Hz), 7.9–7.7(3H,m), 7.59(1H,dd, J=8.5, 8.5 Hz), 7.48(1H,dd,J= 7.7 Hz), 6.95(1H,d,J=8.5 Hz), 3.95(3H,s), 3.83(3H,s)

Example 1
3-(3-cyclopentyloxy-4-methoxyphenylcarboxylamido)-1H-4-pyrazolecarboxylamide 10 ml of pyridine was added dropwise to 680 mg of 4-amino-1H-5-pyrazolcaroboxyamide to form a suspension. 1.5 g of 3-cyclopentyloxy-4-methoxybenzolic acid chloride was added dropwise to the suspension and was stirred for 1 day. The reaction solution was concentrated under reduced pressure, diluted with chloroform and washed with 1N hydrochloric acid, saturated sodium carbonate and sodium chloride in succession. The organic layer was dried and concentrated under reduced pressure. Column chromatography affored 1.1 g of the title compound.

1H NMR(DMSO-d$_6$, δ): 13.32(1H,brs), 11.41(1H,brs), 8.01(1H,brs), 7.82(1H,brs), 7.53(1H,d,J=7.5H), 7.41(1H,d, J=7.5), 5.0–4.9(1H,m), 3.83(3H,s), 2.1–1.8(2H,m), 1.8–1.6 (2H,m), 1.6–1.5(2H,m)

Example 2

4-(3-cyclopentyloxy-4-methoxyphenylcarboxylamido)-2-thiophencarboxylamide 10 ml of pyridine was added dropwise to 680 mg of 4-amino-5-imidazolecaroboxyamide hydrochloride to form a suspension. 1.5 g of 3-cyclopentyloxy-4-methoxybenzolic acid chloride was added dropwise to the suspension and was stirred for 1 day. The reaction solution was concentrated under reduced pressure, diluted with chloroform and washed with 1N hydrochloric acid, saturated sodium carbonate and sodium chloride in succession. The organic layer was dried and was concentrated under reduced pressure. Column chromatography affored 1.2 g of the title compound.

1H NMR(CDCl$_3$, δ): 10.96(1H,brs), 7.51(1H,d,J=8.5 Hz), 7.43(1H,brs), 7.5–7.4(1H, m), 7.14(1H,d,J=8.5 Hz), 4.9–4.8(1H,m), 3.88(3H,s), 2.0–1.8(2H,m), 1.8–1.7(4H,m), 1.7–1.6(2H,m)

Example 3

4-(3-cyclopentyloxy-4-methoxyphenylcarboxylamido)-2-thiophencarboxylamide 10 ml of pyridine was added dropwise to 600 mg of 3-amino-2-thiophenylcaroboxyamide to form a suspension. 1.5 g of 3-cyclopentyloxy-4-methoxybenzolic acid chloride was added dropwise to the suspension and was stirred for 1 day. The reaction solution was concentrated under reduced pressure, diluted with chloroform and washed with 1N hydrochloric acid, saturated sodium carbonate and sodium chloride in succession. The organic layer was dried and was concentrated under reduced pressure. Column chromatography affored 1.2 g of the title compound.

1H NMR(DMSO-d$_6$, δ): 12.42(1H,brs), 8.11(1H,d,J=5.5 Hz), 7.84(1H,d,J=5.5 Hz), 7.51(1H,dd,J=8.5,2 Hz), 7.45 (1H,d,J=2), 7.14(1H,d,J=2), 7.14(1H,d,J=8.5 Hz), 5.0–4.8 (1H,m), 3.84(3H,s), 2.1–1.9(2H,m), 1.9–1.7(4H,m), 1.7–1.6 (2H,m)

Example 4

2-(3-cyclopentyloxy-4-methoxyphenyl)-3,4-dihydrothieno[3,4-d]pyrimidine-4-one 25 ml of 1N sodium chloride and 5 ml of ethyl alcohol were added dropwise to 500 mg of 3-(3-cyclopentyloxy-4-methoxyphenylcarboxylamide)-2-thiophenylcarboxylamide, stirred for 4 hours and concentrated under reduced pressure. The reactant was acidified by adding dropwise 1N hydrochloric acid and was filtered with distilled water to obtain 390 mg of the title compound.

$^1$H NMR(DMSO-d$_6$, δ): 12.56(1H,brs), 8.19(1H,d,J=5 Hz), 7.81(1H,dd,J=8.5, 2 Hz), 7.75(1H,d,J=2 Hz), 7.44(1H, d,J=5 Hz), 7.10(1H,d,J=8.5 Hz), 5.0–4.8(1H,m), 3.83(3H, s), 2.0–1.8(2H,m), 1.8–1.6(4H,m), 1.6–1.5(2H,m)

Example 5

2-(3-cyclopentyl-4-methoxyphenyl)-6,7-dihydro-1H-6-purinone 500 mg of 4-(3-cyclopentyloxy-4-methoxyphenylcarboxylamide)-1N-imidazole-5-carboxylamide obtained by Reference Example 6 was reacted in the same manner as Example 1 to obtain 380 mg of the title compound.

$^1$H NMR(DMSO-d$_6$, δ): 12.60(1H,brs), 8.61(1H,s), 7.78 (1H,dd,J=8.5, 2 Hz), 7.72 (1H,d,J=2 Hz), 7.11(1H,d,J=8.5 Hz), 5.1–4.9(1H,m), 3.84(3H,s), 2.1–1.9(2H,m), 1.9–1.7 (4H,m), 1.7–1.5(2H,m)

Example 6

5-(3-cyclopentyloxy-4-methoxyphenylcarboxylamildo)-6.7-dihydro-1H-pyrazolo[4,3-d]pyrimidine-7-one 500 mg of 3-(3-cyclopentyloxy-4-methoxyphenylcarboxylamide)-1N-4-pyrazolecarboxylamide obtained by Reference Example 6 was reacted in the same manner as Example 1 to obtain 300 mg of the title compound.

$^1$H NMR(DMSO-d$_6$, δ): 12.62(1H,brs), 8.63(1H,s), 7.77 (1H,dd,J=8.5, 2 Hz), 7.73(1H,d,J=2 Hz), 7.18(1H,d,J=8.5 Hz), 5.1–4.9(1H,m), 3.85(3H,s), 2.1–1.9(2H,m), 1.9–1.7 (4H,m), 1.7–1.5(2H,m)

Example 7

2-(3-cyclopentyloxy-4-methoxyphenyl)-3,4-dihydro-4-quinazolinone 500 mg of (3-cyclopentyloxy-4-methoxyphenylcarboxylamide)benzylamide obtained by Reference Example 6 was reacted in the same manner as Example 1 to obtain 410 mg of the title compound.

$^1$H NMR(DMSO-d$_6$, δ): 12.45(1H,brs), 8.13(1H,d,J=7 Hz), 8.0–7.8(3H,m), 7.70(1H, dd,J=8.5 Hz), 7.48(1H,dd,J= 7, 7 Hz), 7.10(1H,d,J=8.5 Hz), 5.0–4.9(1H,m), 3.83(3H,s), 2.1–1.9(2H,m), 1.9–1.7(4H,m), 1.7–1.5(2H,m)

Example 8

3-(3,4-dimethoxyphenylcarboxylamido)-3,4-dihydro-4-quinazolinone 500 mg of 3,4-dimethoxyphenylcarboxylamide obtained by Reference Example 7 was reacted in the same manner as Example 1 to obtain 400 mg of the title compound.

$^1$H NMR(CDCl$_3$, δ): 12.40(1H,brs), 8.10(1H,d,J=7 Hz), 8.0–7.8(3H,m), 7.67(1H,dd, J=8.5 Hz), 7.42(1H,dd,J=7, 7 Hz), 7.05(1H,d,J=8.5 Hz), 3.92(3H,s), 3.80(3H,s)

EXPERIMENTAL EXAMPLES

I. Passive Cutanious Anaphylaxis (PCA)

Hair on the back of each of the three 5 weeks old female Wistar rats were cut by clippers. Prepared mouse antiserum was diluted with 50×physiological saline solution. 0.05 ml of diluted antiserum solution was subcutaneously injected into two hair-cut sites on the back of each rat. After 3 hours, the test compounds were orally administered to the rats. After 30 minutes, 0.1% ovalbumin as antigen was mixed with 1% evans blue in the equivalent volumes and 0.1 ml of the mixture was injected in a peripheral vein of the tail of each rat. After 30 minutes, rats were sacrificed by bleeding from the abdominal arteries and their skins were stripped from the subcutaneous injection spots in uniform sizes. After immersing the stripped skins in 1.0 ml of 1.2 N KOH in 9 ml test tube and stopping the tube, a shaking incubation was performed at 37° C. for 24 hours. Then, after the mixtured solution of acetone and 0.6 N phosphoric acid (13:5) was added, the test tube was shaking-incubated for 1 hour and centrifuged to 1,700 g at 20° C. for 10 minutes. After insoluble lipids were removed from the top of the supernatant, the supernatant was measured at 620 nm. IgE was quantified by diluting the mixtured acetone-phosphoric aicd solution and drawing evans blue assay lines. The results are shown in Table I below, in which the amounts of IgE were expressed as μg/ml.

TABLE I

| | Test Compound | |
|---|---|---|
| Dose (mg/rat) | Example 1 | Example 2 |
| 0.1 | 4.578 | 3.381 |
| 2.0 | 4.099 | 2.694 |

II. Inhibition of Phosphodiesterase IV Activity

Phosphodiesterase I, II, III, IV or V partially purified from human U937 cells, test compound of Example 1, 2 or 3 and 1.0 μM cAMP including μM [$^3$H] cAMP were incubated at 30° C. for 20 minutes. The PDE reaction to convert cAMP into AMP was completed by boiling the reaction solution for 2 minutes. AMP was converted into adenosine by adding snake venom nucleotidase and incubating the reaction solution for 10 minutes. While unhydrolyzed cAMPs were bonded to AG1-X2 resin, the aqueous remaining [$^3$H] adenosine was quantified by scintillation counting. The results are shown in Table II below, in which the values indicate inhibition(%) of each PDE by each test compound.

TABLE II

| | Phosphodiesterase Type | | | | |
|---|---|---|---|---|---|
| Test Compound | I | II | III | IV | V |
| Example 1 | 58 | 65 | 68 | 90 | 89 |
| Example 2 | 68 | 60 | 67 | 80 | 61 |
| Example 3 | 67 | 68 | 74 | 90 | 69 |

What is claimed is:

1. A compound of the general formula I:

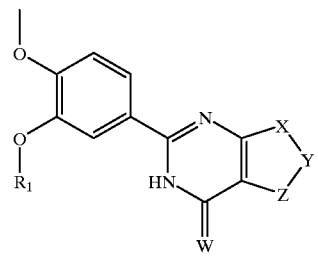

Formula I or a pharmaceutically acceptable salt thereof in which

R1 is $C_{1-7}$ alkyl; $C_{3-7}$ cycloalkyl; phenyl optionally substituted with lower alkyl, lower alkoxy, nitro or halogen; pyrimidinyl optionally substituted with lower alkyl, lower alkoxy, nitro or halogen; or pyridinyl optionally substituted with lower alkyl, lower alkoxy, nitro or halogen;

X is nitrogen, Y is CH, X and Y are connected by a double bond, and Z is $NR_2$;

W is oxygen or sulfur; and $R_2$ is $C_{1-6}$ alkyl, $C_{3-6}$ cycloalkyl or phenyl.

2. The compound of claim 1 wherein $R_1$ is methyl or cyclopentyl; and W is oxygen.

3. The compound of claim 1 which is 2-(3-cyclopentyloxy-4-methoxyphenyl)-6,7-dihydro-1H-6-purinone.

4. A pharmaceutical composition comprising a pharmaceutically acceptable amount of the compound according to claim 1 and a pharmaceutically acceptable carrier.

* * * * *